United States Patent [19]

Busch

[11] Patent Number: Plant 6,055

[45] Date of Patent: Dec. 8, 1987

[54] VARIETY OF GERANIUM NAMED DANIELLE

[75] Inventor: Daniel T. Busch, Thornton, Colo.

[73] Assignee: Busch Greenhouses, Inc., Denver, Colo.

[21] Appl. No.: 807,172

[22] Filed: Dec. 9, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new geranium cultivar is characterized by its brilliant color and a short and compact plant. A short flower stem positions the flower immediately atop of the foliage and renders the plant very resistant to wind and rain damage. The pink coloring is accentuated by a red blotch in the throat and a white eye in the center of the floret.

1 Drawing Figure

BACKGROUND OF THE NEW PLANT

The present invention comprises a new and distinct cultivar of *Pelargonium hortorum*, Bailey known by the varietal name Danielle. The new variety was discovered in the spring of 1985 as a sport of the cultivar Veronica, U.S. Plant Pat. No. 5,054.

The new cultivar was discovered by Daniel T. Busch at Busch Greenhouses, Inc. in Denver, Colo., was sexually reproduced by cuttings at Busch Greenhouses, Inc., and has been repeatedly asexually reproduced by cuttings at Oglevee Associates, Inc. in Connellsville, Pa. It has been found to retain its distinctive characteristics through successive propagations. The new cultivar differs from the cultivar Veronica by its brilliant pink coloring and prolific flowering.

The new cultivar, when grown in a glass greenhouse in Connellsville, Pa. using natural light, 60° F. day temperature and 71° F. vent temperature and grown in a soilless media having constant fertilization at 275 parts per million nitrogen and potassium under normal day and full sunlight conditions, has a response time from a rooted cutting to a flowering plant in a 10 cm pot of six weeks.

DESCRIPTION OF THE DRAWING

The sole photographic drawing illustrates the new cultivar, the color being as nearly true as possible with color illustrations of this type.

DESCRIPTION OF THE NEW PLANT

The following detailed descriptions set forth the characteristics of the cultivar. The data which define these characteristics were collected from asexual reproductions carried out by Oglevee Associates, Inc. in Connellsville, Pa. The plant history was taken on six week plants blossomed under natural light in a greenhouse and color readings were taken indoors under 200 foot candles of cool, white fluorescent light. Color references are primarily to the R.H.S. Colour Chart of The Royal Horticultural Society of London.

THE PLANT

Classification:

*Botanical.*—*Pelargonium hortorum*, Bailey.

*Commercial.*—Zonal geranium.

Form: Short, compact, with free basal branching; closer internodes and small leaves as compared to common zonal geraniums. Blooms 3–5 cm above foliage.

Height: 14–20 cm as a 4 inch pot plant excluding bloom and 24–30 cm as a 4 inch pot plant including bloom.

Growth: Free-branching from base; short internodes with prolific flowering.

Strength: Very sturdy and not susceptible to wind and rain damage. Stands upright without artificial support.

Foliage: Stalked leaf attachment; zoning.

Leaves:

*Size.*—7–10 cm across fully expanded leaves.

*Shape.*—Reniform with cordate base.

*Margin.*—Crenate.

*Texture.*—Leathery and pubescent.

*Color.*—Top: Outer margin — green group. 137B; center — green group 138B. Bottom: Yellow green group 146B.

*Ribs and veins.*—Palmate.

Petioles: Yellow green group 146C; 7–11 cm long.

Stem:

*Color.*—Yellow green group 144C.

*Internodes.*—1–2 cm in length.

THE BUD

Shape: Umbel in form with numerous florets.

Size: As bud develops to color shown, head size is 3 cm in diameter and it opens into a head size of 10 cm in diameter.

INFLORESCENCE

Blooming habit: Continuous throughout year.

Size: 10 cm in diameter and 6 cm in height.

Borne: Singly in an umbel form.

Florets:

*Form.*—Flat to slightly cupped; slightly asymmetrical in shape; slightly ruffed edge.

*Color.*—Throat: White with red purple markings. Top: Outer petal red purple group 67C; inner zone red purple group 66A. Bottom: Red purple group 68C.

*Petals.*—7–9 in number plus 2–6 petaloids.

*Size.*—3–4 cm diameter.

*Texture and appearance.*—Firm and satiny.

Petaloids:

*Quantity.*—2–6.

*Shape.*—Irregular.

*Color.*—Top: Red purple group 67C. Bottom: Red purple group 62B.

Pedicel:

*Length.*—1–2 cm in length.

Peduncle: 17–20 cm in length; arise from node opposite leaf node.

*Color.*—Yellow green group 144B.

Persistence: Non-shattering flower.

Disease resistance: Good Botrytis resistance.

Lasting quality: Up to three weeks.

REPRODUCTIVE ORGANS

Stamens:

*Anthers.*—6–8.

*Filaments.*—White base with pinkish tip; irregular in shape; some petaloid formation; flat at base, twisted at top; 5–7 mm in length.

*Pollen.*—Pinkish-orange initially, brownish-orange when mature.

Pistils:

*Number.*—1 with 5 parted stigma.

*Length.*—8 mm.

*Stigma.*—5 parted; pinkish in color.

*Style.*—Pinkish; 1–2 mm in length.

Ovaries: 4 mm in length; yellow green in color.

Fruit: None observed.

The new cultivar is characterized by its brilliant color and a short and compact plant. There is more basal branching, close internodes, and smaller leaves as compared with standard bush zonal geraniums produced in the United States. A short flower stem positions the flower immediately atop of the foliage into plants and renders the plant very resistant to wind and rain damage. The brilliant pink coloring is accentuated by the red blotch in the throat and the white eye in the center of the floret.

I claim:

1. A new and distinct variety of geranium plant substantially as herein shown and described and parts therefor.

* * * * *

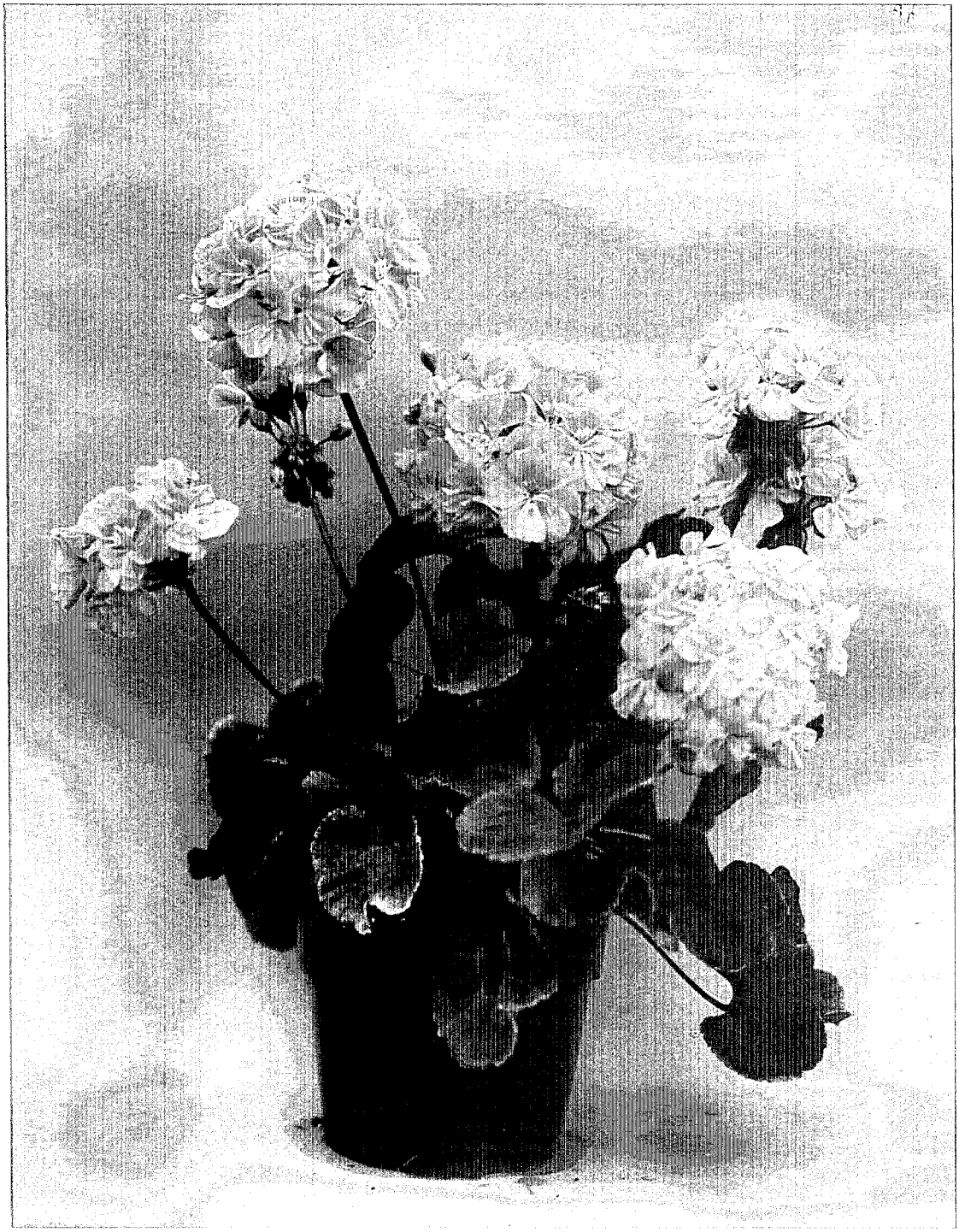

UNITED STATES PATENT AND TRADEMARK OFFICE

CERTIFICATE OF CORRECTION

PATENT NO. : PP 6055

DATED : December 8, 1987

INVENTOR(S) : Daniel T. Busch

It is certified that error appears in the above-identified patent and that said Letters Patent is hereby corrected as shown below:

Column 1 Lines 9 and 10 "was sexually" should read

—was first asexually—.

Signed and Sealed this

Twenty-fourth Day of May, 1988

*Attest:*

DONALD J. QUIGG

*Attesting Officer*

*Commissioner of Patents and Trademarks*